United States Patent [19]
Payza et al.

[11] Patent Number: 5,908,832
[45] Date of Patent: Jun. 1, 1999

[54] PEPTIDE ANALOG

[75] Inventors: Kemal Payza, Silver Spring, Md.; David H. Malin, Houston, Tex.

[73] Assignee: University of Houston - Clearlake, Houston, Tex.

[21] Appl. No.: 07/771,557

[22] Filed: Oct. 7, 1991

[51] Int. Cl.[6] .............................. A61K 38/04; C07K 5/00; C07K 16/00; C07K 17/00
[52] U.S. Cl. .................. 514/16; 514/17; 514/18; 514/19; 530/328; 530/329; 530/330
[58] Field of Search .................... 514/16, 17–18, 514/19; 530/328, 329, 330

[56] References Cited

PUBLICATIONS

Charpentier, et al, *Peptides*, vol. 9, pp. 835–841, 1988.
Majane, et al, *Peptides*, vol. 8 pp. 657–662, 1987.
Majane, et al *Peptides* vol. 9 pp. 1137–1144, 1988.
Yang, et al *Proc. Natl. Acad. Sci*, vol. 82, pp. 7757–7761, 1985.
Tang, et al, *Proc. Natl. Acad. Sci* vol. 81, pp. 5002–5005, 1984.
Malin et al, *Peptides*, vol. 11, pp. 969–972, 1990.
Malin, et al, *Peptides*, vol. 11 pp. 277–280, 1990.
Payza, et al, *J. Pharmacology and Experimental Therapeutics*, vol. 267, No. 1, pp. 88–94. 1993.
Malin et al, *Life Sciences*, vol. 53. PL 261–266, 1993.

*Primary Examiner*—Cecilia J. Tsang
*Assistant Examiner*—S. G. Marshall
*Attorney, Agent, or Firm*—J. M. (Mark) Gilbreth; Robert W. Strozier; Gilbreth & Strozier, P.C.

[57] ABSTRACT

The present invention relates to an analog of Neuropeptide FF (e.g., daY8Ra) and to a pharmaceutical composition containing same. The invention further relates to methods of using the analog to attenuate the effects of drug addiction, drug tolerance, drug dependence or of abstinence syndrome.

11 Claims, 5 Drawing Sheets

PEPTIDE ANALOG

BACKGROUND OF THE INVENTION

1. Technical Field

The present invention relates to a peptide analog and to methods of using same to attenuate the effects of drug addiction, drug tolerance, drug dependence or of abstinence syndrome.

2. Background Information

The octapeptide NPFF (Phe-Leu-Phe-Gln-Pro-Gln-Arg-Phe-amide (SEQ ID NO:1)-amide) was originally isolated by Yang et al from bovine brain (Yang et al, Proc. Natl. Acad. Sci., 82:7757–7761 (1985)). It has also been referred to as "morphine-modulating peptide" or "FMRF-$NH_2$-like mammalian octapeptide" (Panula et al, Med. Biology, 65:127–35 (1987)) or Neuropeptide FF (Kivipelto et al, Journal of Comparative Neurology). There are reasons to suspect that NPFF may be an "anti-opiate peptide": NPFF is localized in several brain regions rich in endogenous opioids (Ferrarese et al, Regulatory Peptides, 13:245–52 (1986); Panula et al, Med. Biology, 65:127–35 (1987)), is released from the brain by morphine infusion (Tang et al, Proc. Natl. Acad. Sci., 81:5002–5 (1984)), and potently antagonizes analgesic effects of morphine and certain endogenous opioid peptides (Tang et al, Proc. Natl. Acad. Sci., 81:5002–5 (1984); Yang et al, Proc. Natl. Acad. Sci., 82:7757–7761 (1985); Yang et al, Prog. Clin. Biol. Res., 192:313–22 (1985)). IgG from NPFF antiserum augments morphine and stress-induced analgesia (Kavaliers et al, Peptides, 10:741–5 (1989)).

There is also evidence that NPFF may participate in opiate tolerance and dependence. IgG prepared from FMRFa antiserum cross-reacts with NPFF and interferes with morphine tolerance (Tang et al, Proc. Natl. Acad. Sci., 81:5002–5 (1984)). NPFF levels in CSF are markedly increased in opiate dependent rats as compared with non-dependent rats (Malin et al, Peptides, 11:969–972 (1990)). NPFF (2 μg i.c.v.) precipitates opiate abstinence syndrome in morphine-dependent rats (Malin et al, Peptides, 11:277–280 (1990)), and NPFF (15 μg i.c.v.) induces a quasi-morphine-abstinence syndrome (QMAS) in opiate-naive rats (Malin et al, Peptides, 11:277–280 (1990)) (see also Guzman et al, Neuropeptides 14:253–261 (1989); Majane et al, Peptides, 8:657–662 (1987); Majane et al, Peptides, 9:1137–1144 (1988)). Third ventricle infusion of IgG from NPFF antiserum reverses opiate dependence, as evidenced by prevention of naloxone-precipitated abstinence syndrome in morphine-dependent rats (Malin et al, Peptides, 11:969–972 (1990)). The mechanism of action of NPFF is not understood as yet, but a recent receptor binding study in spinal cord membranes suggested that the neuropeptide binds to specific NPFF receptors. The $^{125}$I-Y8Fa binding site showed high affinity for NPFF, whereas opioid ligands failed to compete for binding (Allard et al, Brain Research, 500:169–176 (1989)).

Applicants recognized that an NPFF antagonist peptide would be useful as a probe for determining the physiological role of endogenous NPFF, as well as further ascertaining its role in opiate dependence, tolerance and abstinence. Accordingly, a NPFF analog was synthesized. A preferred embodiment of this analog differs in two respects from the NPFF sequence. First, in order to reduce receptor activation, the C-terminal Arg-Phe-amide is replaced by Arg-amide. Secondly, in order to increase resistance to aminopeptidase, the N-terminal is blocked with desaminotyrosine (daY). With both N-and C-terminals blocked, this peptide has increased enzyme resistance and receptor availability. DaY increases peptide binding affinity at molluscan FMRFa receptors and it was for this reason that it was added (see Payza, Peptides, 8:1065–1074 (1987)).

The analog of the invention is useful in acting as an antagonist in blocking the effects of NPFF, and in acting to block dependence on drugs of abuse or addiction and their subsequent abstinence syndromes. The present invention provides a method by which the NPFF analog can be employed to either enhance the efficacy of morphine treatment or to prevent drug dependence and to ameliorate the effects of abstinence syndromes.

SUMMARY OF THE INVENTION

It is a general object of the invention to provide a peptide analog of NPFF and method of using same to attenuate the effects of drug addiction, drug tolerance and abstinence syndrome. It is a particular object of the invention to provide a method of attenuating the effects of opiate addiction, tolerance, dependence or abstinence syndrome. An analog of the invention comprises an amino acid sequence selected from the group consisting of: X-TYR-PHE-LEU-PHE-GLN-PRO-GLN-ARG-Y (X-(SEQ ID NO:2)-Y), X-PHE-LEU-PHE-GLN-PRO-GLN-ARG-Y (X-(SEQ ID NO:3)-Y), X-LEU-PHE-GLN-PRO-GLN-ARG-Y (X-(SEQ ID NO:4)-Y), X-PHE-GLN-PRO-GLN-ARG-Y (X-(SEQ ID NO:5)-Y), X-GLN-PRO-GLN-ARG-Y (X-(SEQ ID NO:6)-Y), X-PRO-GLN-ARG-Y, X-GLN-ARG-Y and X-ARG-Y, wherein X is a pharmaceutically acceptable hydrophobic group and Y is an amide group unsubstituted or mono- or di-substituted with a $C_{1-4}$ alkyl or benzyl group.

DETAILED DESCRIPTION OF THE INVENTION

Figure 1:
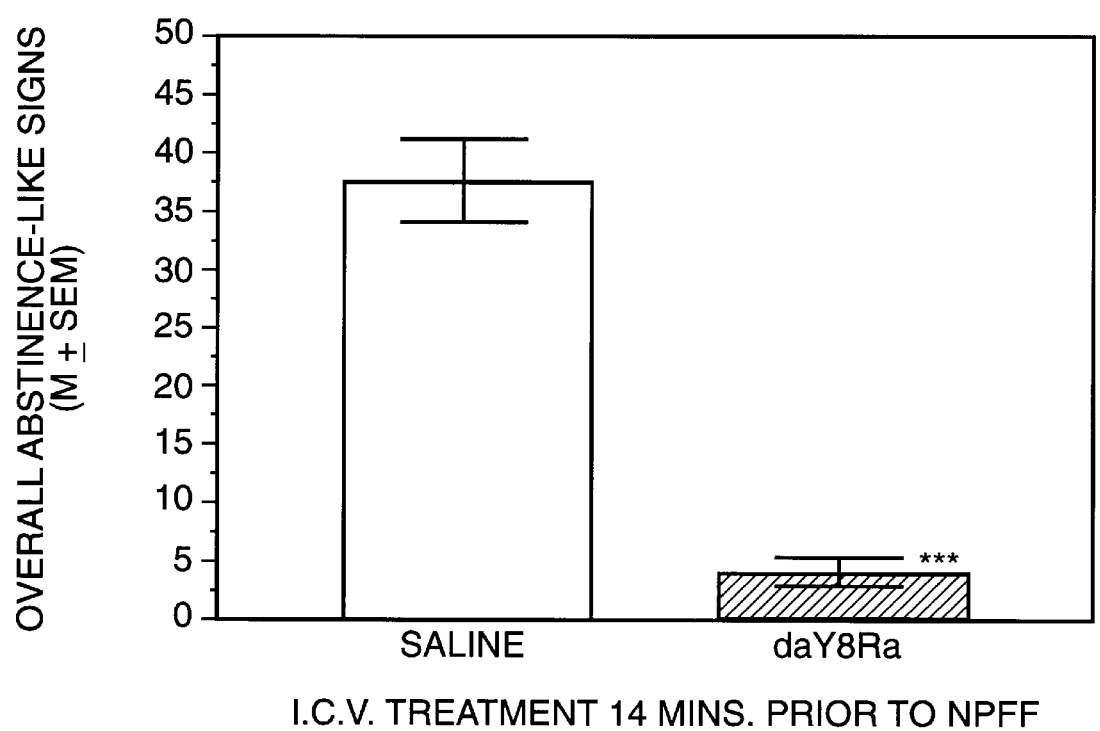
FIG. 1 demonstrates that pretreatment with daY8Ra (600 ng i.c.v.) prevents quasimorphine abstinence syndrome induced by NPFF (10 μg i.c.v.) in opiate-naive rats. The symbol *** represents p<0.001 vs. saline.

The present invention relates, in one embodiment, to the peptide desaminoYFLFQPQRamide (daY8Ra), which has been found to be useful, for example, in alleviating opiate dependence, as evidenced by blocking the subsequent abstinence syndrome, as well as the subsequent effects of abstinence syndrome. The daY8Ra peptide is an analog of the octapeptide FLFQPQRFamide (NPFE, (SEQ ID NO:1)), a neuropeptide believed to be involved in opiate tolerance and dependence and in the precipitation of abstinence syndrome upon discontinuance of opiate use.

DaY8Ra constitutes a preferred embodiment of the present invention and indeed the disclosure of the invention is largely described with reference thereto. However, the invention is broader than this embodiment and includes within its scope fragments of daY8Ra that contain the active C-terminal arginine, modified forms of daY8Ra including non-peptide drugs that mimic the effect of daY8Ra as well as modified peptides. This latter class includes peptides with enhanced ability to cross the blood-brain barrier, for example: (a) peptides that consist of fewer amino acids than daY8Ra but that retain the active C-terminal fragment ending in Arg-amide, e.g., QPQR-amide, (SEQ ID NO:6)-amide; (b) peptides that have one or both of the hydrogens at the C-terminal amide substituted with hydrophobic alkyl groups, preferably a $C_{1-4}$ alkyl group (for example, the amide can be replaced with diethylamide or propylamide); (c) peptides wherein the hydrogens at the peptide bonds are replaced by methyl groups; and (d) peptides wherein hydrophobic groups are added to replace the daY at the amino terminal of the peptide, such as an ethanoyl (acetyl), propanoyl, butanoyl, pentanoyl, hexanoyl, heptanoyl, benzoyl, dansyl or t-boc group; other acyl or alkyl groups can also be used.

In addition to the foregoing, the invention also relates to forms of daY8Ra modified so as to be resistant to degradation by endogenous peptidase. For example, such peptides can have D-amino acids substituted for the L-amino acids or peptide hydrogens substituted by methyl groups. Retro-inverso peptide bonds between one or more pairs of adjacent amino acid residues can also be used to block degradation. (Retro-inverso bonds have been used successfully to make enzyme-resistant CCK analogs. (Charpentier et al, 1988, Peptides 9:835–841.)) In addition, groups other than daY can be used to block the N-terminal amino group so as to prevent degradation by aminopeptidases.

DaY8Ra itself constitutes an NPFF antagonist whereby modifications are made at both the C-terminal and the N-terminal of the NPFF peptide. The first modification to NPFF is made at the C-terminus, where the Arg-Phe-amide is replaced by Arg-amide in order to reduce receptor activation. Secondly, the addition of desaminotyrosine (daY) is made to the N-terminus in order to provide resistance to aminopeptidase. Moreover, the daY addition is intended to increase binding affinity of the peptide for the receptor. The combined effect of blocking the C- and N-termini is to increase enzyme resistance and receptor availability.

A method of making daY8Ra is detailed in the Examples that follow. Modified forms of daY8Ra, referenced above, can be synthesized by adapting appropriate techniques known in the art.

A second embodiment of the invention relates to a composition which includes, as the active ingredient, any of the forms of the peptide analog described above in combination with a pharmaceutically acceptable carrier. Suitable carriers can be readily determined by one skilled in the art and such an artisan can readily determine optimum concentrations of the peptide to be included in the composition. One skilled in the art will appreciate that the composition to which the invention relates can contain further components including stabilizers, such as peptidase inhibitors to prevent degradation of the peptide.

A third embodiment of the invention relates to a method of using the peptide analog to antagonize the activity of NPFF and thereby attenuate the effects of drug addiction, drug tolerance or of abstinence syndrome. In a specific embodiment, the invention relates to a method of using the peptide analog to reduce a patient's dependence on opiates or opioids. In accordance with this aspect of the invention, one skilled in the art will appreciate that the amount of the active peptide to be administered can be optimized to suit a particular patient's needs, taking into account the treatment protocol used. However, it is contemplated that doses of 0.1 to 20 μg/kg b.w., preferably 1–2 μg/kg b.w. can be used, for example, when intrathecal injection into the third ventricle is the route of administration. When intravenously injected, higher doses can be expected to be required. The optimum frequency of administration can be readily determined by one skilled in the art.

Specific aspects of the invention will be illustrated in greater detail by reference to the non-limiting Examples that follow.

EXAMPLES

The experimental details that follow are referenced in the specific Examples set forth below:

Subjects

The subjects were 44 male Sprague-Dawley rats weighing 325–375 grams, maintained on a 12 hour light/dark cycle and on ad lib food and water. Each rat was stereotaxically cannulated in the third ventricle under equithesin anesthesia. Cannula placements were subsequently confirmed by injection of methylene blue dye.

Drugs and Injections

DaY8Ra was custom-synthesized by Multiple Peptides Systems (San Diego, Calif.). The analog daY9Fa was made by reacting Bolton-Hunter reagent (Fluka, Ronkonkoma, N.Y.) with NPFF in DMF, followed by separation by reverse phase HPLC. The method was adapted from that used to make daYFnLRFa (Payza et al., Peptides, 8:1065–1074 (1987)). Morphine sulfate and naloxone HCl were donated by the NIDA Research Support Branch.

Drugs for third ventricle injection were dissolved in isotonic saline. All injections were carried out by motorized syringe at the rate of 4 μl/min. Optimal time intervals between i.c.v. injections were determined by small pilot experiments.

Example I

Ability of daY8Ra to Antagonize the Behavioral Effects of NPFF in Opiate-Naive Rats Experiment 1 tested whether daY8Ra could antagonize the behavioral effects of NPFF in opiate-naive rats. Seven days following cannulation, 12 rats were randomly divided into two treatment groups of six rats each. Each rat received a third ventricular injection of either 600 ng daY8Ra in 30 μl saline or saline alone. Small pilot experiments determined that this dose of daY8Ra antagonized actions of NPFF without itself inducing NPFF-like effects; doses of 2–24 μg appeared, like NPFF, to precipitate some opiate abstinence signs in morphine-dependent rats.

Fourteen minutes after completion of the daY8Ra or saline injections, all rats received 10 μg NPFF (Peninsula Laboratories, Belmont, Calif.) in a vehicle of 0.06 μg bestatin (Peninsula Laboratories) in 30 μl saline. Similar doses of NPFF have previously been shown (Malin et al, Peptides, 11:277–280 (1990)) to induce a quasimorphine-abstinence syndrome (QMAS). The aminopeptidase inhibitor bestatin was used to prevent enzymatic degradation of the peptide (Tang et al, Proc. Natl. Acad. Sci., 81:5002–5 (1984)).

Each rat was observed for 12 minutes under "blind" conditions for any abstinence-like behavioral signs, commencing with the onset of the daY8Ra or saline injection. Each rat was observed again for 20 minutes commencing with the onset of the NPFF injection. A standard tally sheet of withdrawal signs based primarily on Gianutsos et al. (Gianutsos et al., In: Ehrenpreis, S.; Neidle, A., eds. Methods in Narcotic Research. New York; Marcel Dekker (1975) 293) was employed. The overall score for each rat was the total frequency of observed abstinence-like signs across all categories.

There were very few abstinence-like signs following the daY8Ra injection, 3.00±0.72 (M±SEM), or saline injection 4.00±1.02. The difference between the two groups was not significant, $t(10)=0.62$, NS.

Following the NPFF injection, the group pretreated with saline responded with a vigorous quasi-morphine-abstinence syndrome, while the group pretreated with daY8Ra had approximately 90% fewer overall abstinence-like signs (FIG. 1). This difference was highly significant, $t(10)=7.20$, $p<0.001$.

Figure 2:
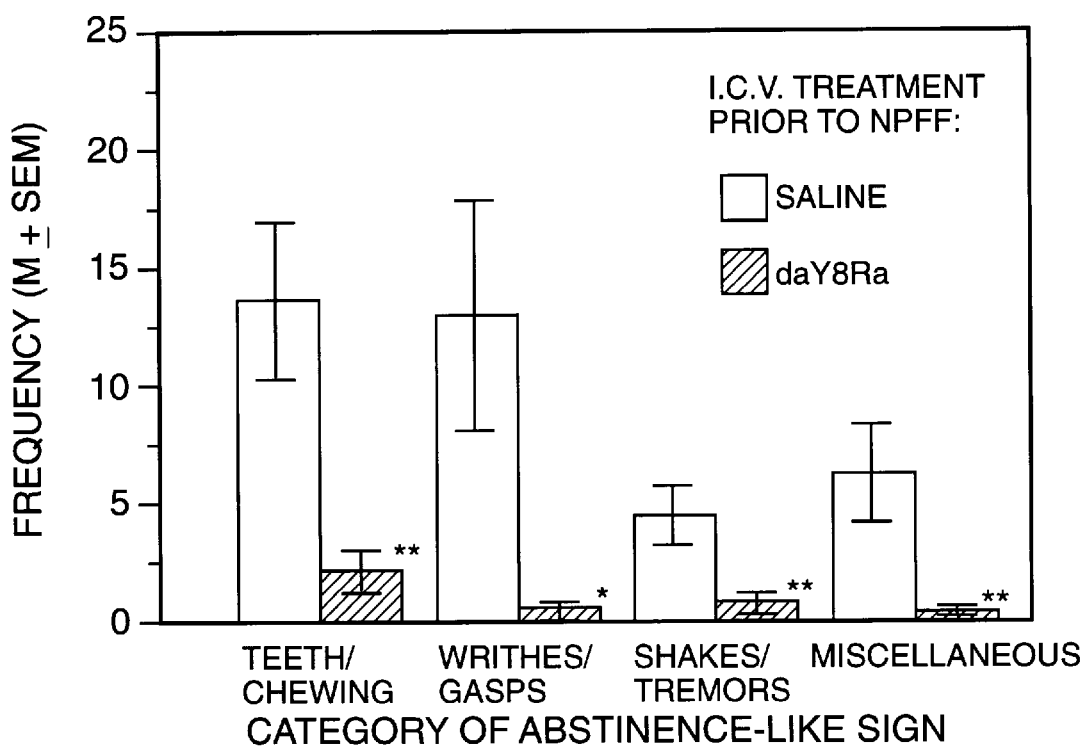
FIG. 2 shows that pretreatment with daY8Ra (600 ng i.c.v.) reduces the frequency of various categories of abstinence-like signs induced by NPFF (10 μg i.c.v.). The symbol * represents p<0.05, and ** represents p<0.01 vs. saline.

FIG. 2 shows the frequencies of particular categories of abstinence-like signs. Pretreatment with daY8Ra resulted in significantly lower frequencies of shakes/tremors, $t(10)=2.78$, $p<0.01$, writhes/gasps $t(10)=2.31$, $p<0.05$, teeth chatter/chewing, $t(10)=3.31$, $p<0.01$ and miscellaneous less frequent signs (scratching, ptosis, seminal ejaculation, ataxia, dyspnea), $t(10)=2.86$, $p<0.01$.

Example II

Ability of daY8Ra to Prevent Naloxone-Precipitated Abstinence in Morphine-Dependent Rats Experiment 2 determined whether daY8Ra, could prevent naloxone-precipitated abstinence in morphine-dependent rats. Fourteen rats were subcutaneously implanted at the time of cannulation with two Alzet 2001 osmotic minipumps and rendered morphine-dependent by seven days continuous infusion of 0.3 mg/kg/hr morphine sulfate. Following the rats way infusion period, rats were randomly divided into two treatment groups of seven rats each. Each rat received a third ventricular injection of either 600 ng daY8Ra in 30 $\mu$l saline or saline alone. Twenty-eight minutes after conclusion of the above injections, all rats were challenged by 10 $\mu$g naloxone HCl in 30 $\mu$l saline i.c.v.

Each rat was observed for 14 minutes under "blind" conditions for standard abstinence signs, commencing with the onset of the daY8Ra or saline injection. Each rat was subsequently observed for 20 minutes, commencing with the onset of naloxone challenge.

Figure 3:
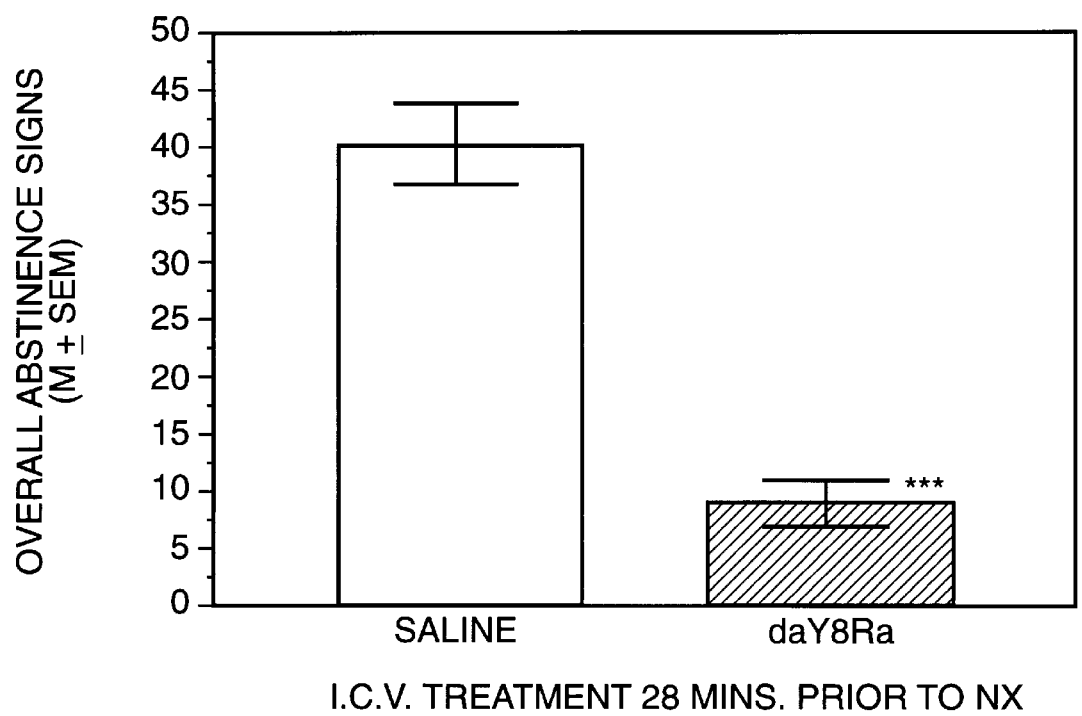
FIG. 3 demonstrates that pretreatment with daY8Ra (600 ng i.c.v.) attenuates abstinence syndrome precipitated by naloxone (10 μg i.c.v.) in rats rendered dependent by 7 days continuous infusion of 0.3 mg/kg/hr morphine sulfate s.c. The symbol *** represents p<0.001 vs. saline.
Figure 4:
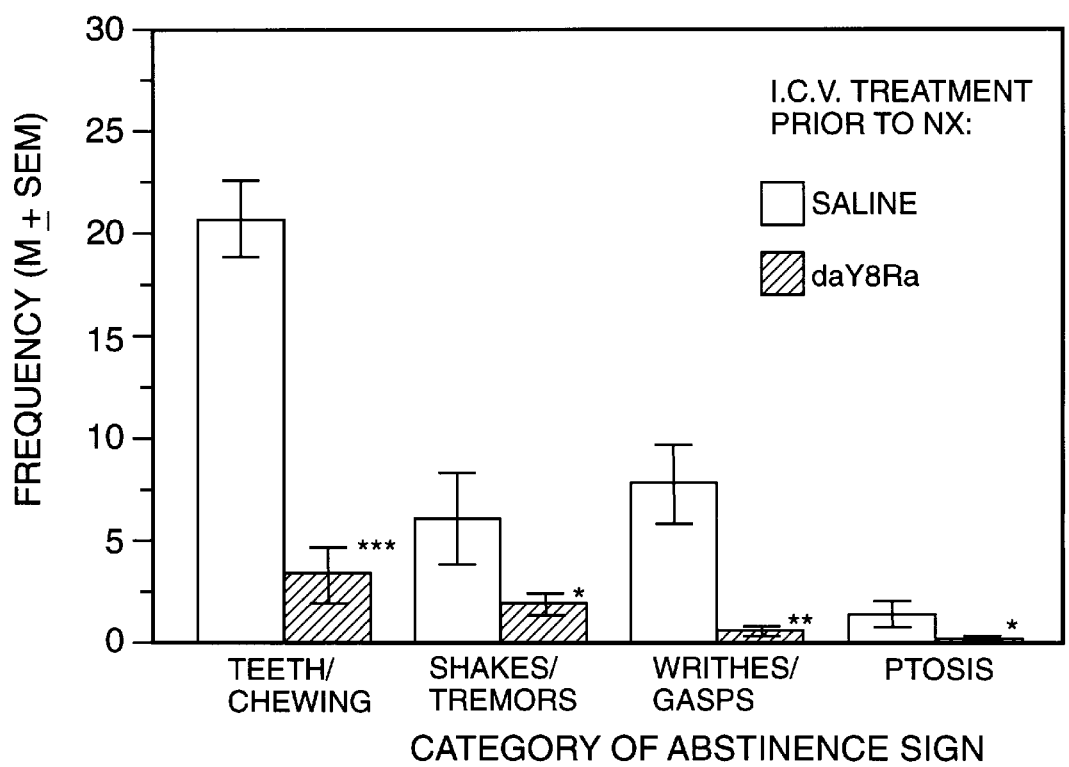
FIG. 4 shows that pretreatment with daY8Ra (600 ng i.c.v.) attenuates frequency of various categories of morphine abstinence signs precipitated by naloxone (10 μg i.c.v.). The symbol * represents p<0.05,  represents p<0.01, and * represents p<0.001 vs. saline.

There were very few abstinence signs following the daY8Ra injection, 4.14±1.55, or the saline injection, 4.00±1.23, and no significant differences between the groups, $t(12)=0.07$, NS. Naloxone precipitated a vigorous abstinence syndrome in saline-pretreated rats. However, rats pretreated with daY8Ra had almost 80% fewer overall abstinence signs than saline-pretreated controls (FIG. 3). This difference was highly significant, $t(12)=7.24$, $p<0.001$. Rats pretreated with daY8Ra had significantly lower frequencies of shakes/tremors, $t(12)=1.90$, $p<0.05$, writhes/gasps, $t(12)=3.81$, $p<0.01$, teeth chatter/chewing, $t(12)=7.43$, $p<0.001$, and ptosis, $t(12)=2.20$, $p<0.5$ (FIG. 4).

Example III

Determination of Whether C-Terminal Modification is Necessary to Prevent Naloxone-Precipitated Abstinence Syndrome This experiment tested whether the C-terminal modification of NPFF is necessary for the prevention of naloxone-precipitated abstinence syndrome. Eighteen rats were rendered morphine dependent as in Experiment 2. Following the seven day morphine infusion period, rats were randomly divided into three equal treatment groups. Each rat received an i.c.v. injection of 600 ng NPFF in a vehicle of 0.06 $\mu$g bestatin in 30 $\mu$l saline, or 600 ng daY9Fa (the N-terminal modified NPFF) in 30 $\mu$l saline, or 30 $\mu$l saline alone.

Twenty-eight minutes after conclusion of the above injections, all rats were challenged by 10 $\mu$g naloxone HCl in 30 $\mu$l saline i.c.v. Each rat was observed under "blind" conditions for standard abstinence signs, for 14 minutes, commencing with the onset of the peptide or saline injections. Each rat was observed again for 20 minutes commencing with the onset of naloxone challenge.

There were very few abstinence signs following the 600 ng NPFF injection, 3.67±0.99, or the saline injection, 2.00±0.77. However, 600 ng of daY9Fa (N-terminal modified NPFF) did precipitate a modest number of abstinence signs, 10.67±2.60. One-way ANOVA revealed a significant difference among the groups, $F(15)=7.59$, $p<0.01$. According to Tukey's HSD Test, the group receiving daY9Fa had significantly more abstinence signs, $p<0.05$, than either of the other two groups.

Figure 5:
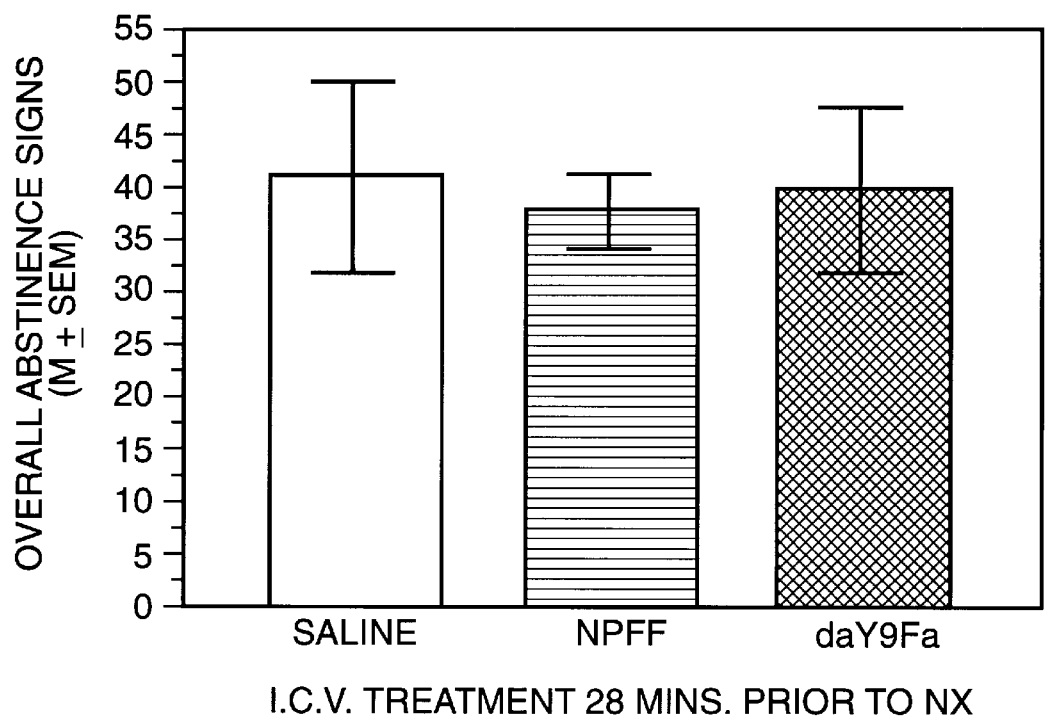
FIG. 5 indicates that pretreatment with NPFF itself (600 ng i.c.v.) or with NPFF modified only at the N-terminal (daY9Fa, 600 ng i.c.v.) does not attenuate abstinence syndrome precipitated by naloxone (10 μg i.c.v.) in rats rendered dependent by 7 days continuous infusion of 0.3 mg/kg/hr morphine sulfate s.c.

Following naloxone challenge, a vigorous abstinence syndrome was precipitated regardless of pretreatment with saline, NPFF or daY9Fa (FIG. 5). One-way ANOVA revealed no significant differences among groups, $F(15)=0.05$, NS.

The references cited above are hereby incorporated, in their entirety, by reference.

One skilled in the art will appreciate from a reading of this disclosure that while certain aspects of the invention have been described in detail for purposes of clarity and understanding, various changes in form and detail can be made without departing from the true scope of the invention.

What is claimed:

1. A peptide consisting essentially of an amino acid sequence selected from the group consisting of:

X-(SEQ ID NO:2)-Y, X-(SEQ ID NO:3)-Y, X-(SEQ ID NO:4)-Y, X-(SEQ ID NO:5)-Y, X-(SEQ ID NO:6)-Y, X-PRO-GLN-ARG-Y, X-GLN-ARG-Y and X-ARG-Y, wherein X is a pharmaceutically acceptable hydrophobic group and Y is an amide group unsubstituted or mono- or di-substituted with a $C_{1-4}$alkyl or benzyl group.

2. The peptide according to claim 1 wherein X is a desamino, acetyl, propanoyl, butanoyl, pentanoyl, hexanoyl, heptanoyl, benzoyl, dansyl or t-boc group.

3. The peptide according to claim 1 wherein at least one of the amino acids of said sequence is a D-amino acid.

4. A peptide consisting essentially of an amino acid sequence selected from the group consisting of:

X-(SEQ ID NO:2)-Y, X-(SEQ ID NO:3)-Y, X-(SEQ ID NO:4)-Y, X-(SEQ ID NO:5)-Y, X-(SEQ ID NO:6)-Y, X-PRO-GLN-ARG-Y, X-GLN-ARG-Y and X-ARG-Y, wherein X is a pharmaceutically acceptable hydrophobic group and Y is an amide group unsubstituted or mono- or di-substituted with a $C_{1-4}$alkyl or benzyl group and wherein at least one peptide bond hydrogen is substituted with a methyl group.

5. The peptide according to one of claims 1 or 4 wherein at least one of the peptide bonds is a retro-inversion peptide bond.

6. A pharmaceutical composition for attenuating the effects of an opiate addiction, opiate dependence, opiate tolerance or opiate related abstinence syndrome, comprising said peptide of one of claims 1 or 5 in an amount sufficient to effect said attenuation, together with a pharmaceutically acceptable carrier.

7. The composition according to claim 6 wherein the composition further comprises an effective amount of at least one peptidase inhibitor.

8. A method of treating an opiate addiction comprising administering to a mammal in need of such treatment an amount of said peptide according to claim 1 sufficient to effect said treatment.

9. A method of treating an opiate dependence comprising administering to a mammal in need of such treatment an amount of said peptide according to claim 1 sufficient to effect said treatment.

10. A method of treating an opiate tolerance comprising administering to a mammal in need of such treatment an amount of said peptide according to claim 1 sufficient to effect said treatment.

11. A method of treating an opiate related abstinence syndrome comprising administering to a mammal in need of such treatment an amount of said peptide according to claim 1 sufficient to effect said treatment.

* * * * *

SEQUENCE LISTING (1) GENERAL INFORMATION:

(iii) NUMBER OF SEQUENCES: 6

(2) INFORMATION FOR SEQ ID NO:1:

```
        (i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:1:

Phe Leu Phe Gln Pro Gln Arg Phe
       1               5

(2) INFORMATION FOR SEQ ID NO:2:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:2:

Tyr Phe Leu Phe Gln Pro Gln Arg
       1               5

(2) INFORMATION FOR SEQ ID NO:3:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:3:

Phe Leu Phe Gln Pro Gln Arg
       1               5

(2) INFORMATION FOR SEQ ID NO:4:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:4:

Leu Phe Gln Pro Gln Arg
       1               5

(2) INFORMATION FOR SEQ ID NO:5:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:5:

Phe Gln Pro Gln Arg
       1               5

(2) INFORMATION FOR SEQ ID NO:6:
```

```
     (i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:6:

Gln Pro Gln Arg
```